US00PP26218P2

(12) United States Plant Patent
Ichie

(10) Patent No.: US PP26,218 P2
(45) Date of Patent: Dec. 15, 2015

(54) ***HYDRANGEA* PLANT NAMED 'KAMOSERE ARIGATOU'**

(50) Latin Name: ***Hydrangea* hybrid**
Varietal Denomination: KAMOSERE ARIGATOU

(71) Applicant: Toyokazu Ichie, Kakegawa (JP)

(72) Inventor: Toyokazu Ichie, Kakegawa (JP)

( * ) Notice: Subject to any disclaimer, the term of this patent is extended or adjusted under 35 U.S.C. 154(b) by 152 days.

(21) Appl. No.: 13/999,414

(22) Filed: Feb. 24, 2014

Related U.S. Application Data

(60) Provisional application No. 61/851,290, filed on Mar. 5, 2013.

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea* plant named 'KAMOSERE ARIGATOU', that is characterized by its upright plant habit, its leaves that are elliptical in shape, its hortensia type inflorescences that are semi-globose in shape, its inflorescences with a larger proportion of sterile flowers with sepals that are elliptical in shape and variegated with centers that are primarily pink with white margins (under alkaline soil conditions with sufficient aluminum) or blue with white margins (under acidic soil conditions).

2 Drawing Sheets

Botanical classification: *Hydrangea* hybrid.
Varietal denomination: 'KAMOSERE ARIGATOU'.

BACKGROUND OF THE INVENTION

The present invention relates to a new and distinct cultivar of *Hydrangea* of hybrid origin and will be referred to hereafter by its cultivar name, 'KAMOSERE ARIGATOU'. 'KAMOSERE ARIGATOU' represents a new *Hydrangea*, a deciduous shrub grown for landscape use.

The new cultivar was derived from a controlled breeding program by the Inventor in Kakegawa-City, Shizuoka, Japan. The Inventor made a cross in 2003 between an unnamed proprietary plant in the Inventor's breeding program; reference no. 00-2A as the female parent and reference no. H1-10 as the male parent. The Inventor selected 'KAMOSERE ARIGATOU' (reference no. 03-19A) as a single unique plant amongst the seedlings that resulted from the above cross in 2005.

Asexual propagation of the new cultivar was first accomplished by stem cuttings in Kakegawa-City, Shizuoka, Japan in July of 2007 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'KAMOSERE ARIGATOU' as a unique cultivar of *Hydrangea*.

1. 'KAMOSERE ARIGATOU' exhibits an upright plant habit.
2. 'KAMOSERE ARIGATOU' exhibits leaves that are elliptical in shape.

3. 'KAMOSERE ARIGATOU' exhibits hortensia type inflorescences that are semi-globose in shape.
4. 'KAMOSERE ARIGATOU' exhibits inflorescences with a large proportion of sterile flowers with sepals that are elliptical in shape and variegated with centers that are primarily pink with white margins (under alkaline soil conditions with sufficient aluminum) or blue with white margins (under acidic soil conditions).

Ref no. 00-2A, the female parent plant of 'KAMOSERE ARIGATOU', differs from 'KAMOSERE ARIGATOU' in having lace-cap type inflorescences and in having sterile flower sepals that are solid in color. Ref No. H1-10, the male parent, differs from 'KAMOSERE ARIGATOU' in having lace-cap type inflorescences. 'KAMOSERE ARIGATOU' can be most closely compared to the cultivars 'Bavaria' (not patented) and 'Tivoli' (not patented). 'Bavaria' and 'Tivoli' are both similar to 'KAMOSERE ARIGATOU' in having inflorescences that are semi-globose in shape and in having multicolored sterile flower sepals with white edges. 'Bavaria' differs from 'KAMOSERE ARIGATOU' in having sterile flower sepals with a higher ratio of multiple colors in sepal centers and in being napiform in shape. 'Tivoli' differs from 'KAMOSERE ARIGATOU' in having sterile flower sepals that are napiform in shape and in having inflorescences that are denser.

BRIEF DESCRIPTION OF THE DRAWINGS

The accompanying colored photographs illustrate the overall appearance and distinct characteristics of the new *Hydrangea*.

The photographs in FIG. 1 and FIG. 2 were taken of a plant about 2 years in age as grown under alkaline soil conditions in a greenhouse in 14-cm containers in Reeuwijk, The Netherlands.

Figure 1:
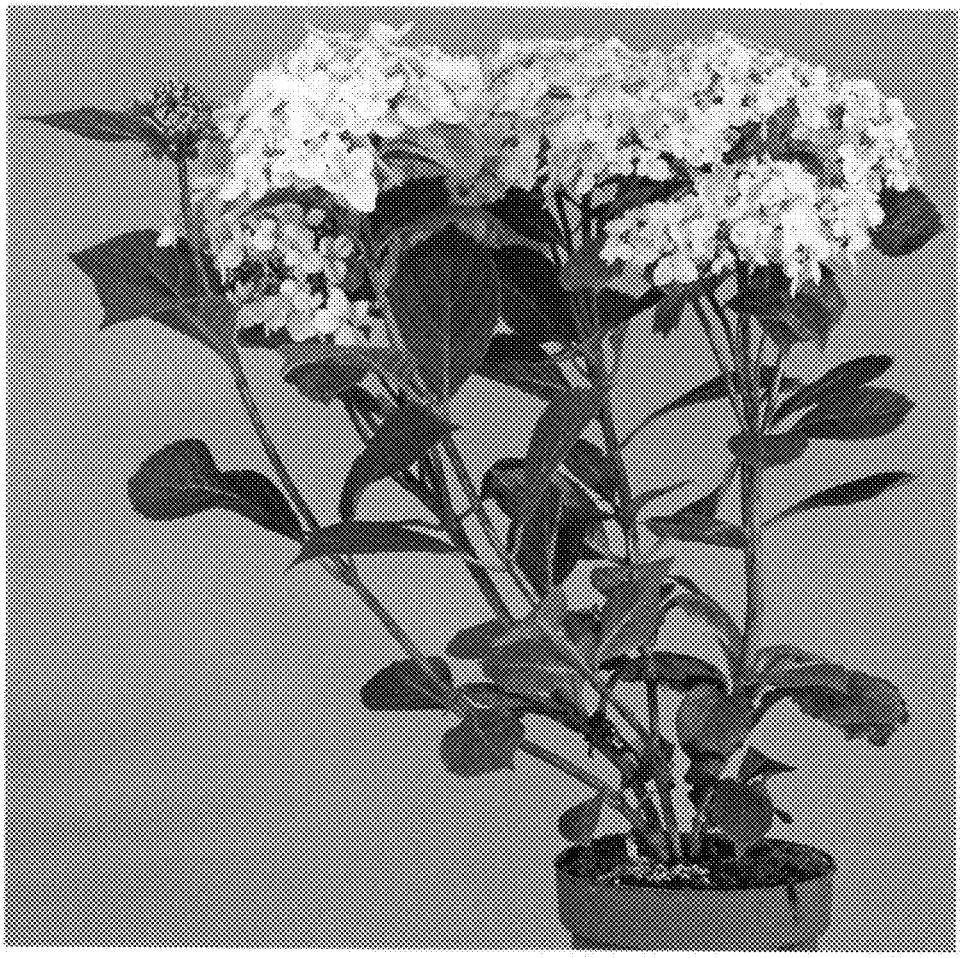

The photograph in FIG. 1 provides a side view of 'KAMOSERE ARIGATOU' in bloom.

Figure 2:
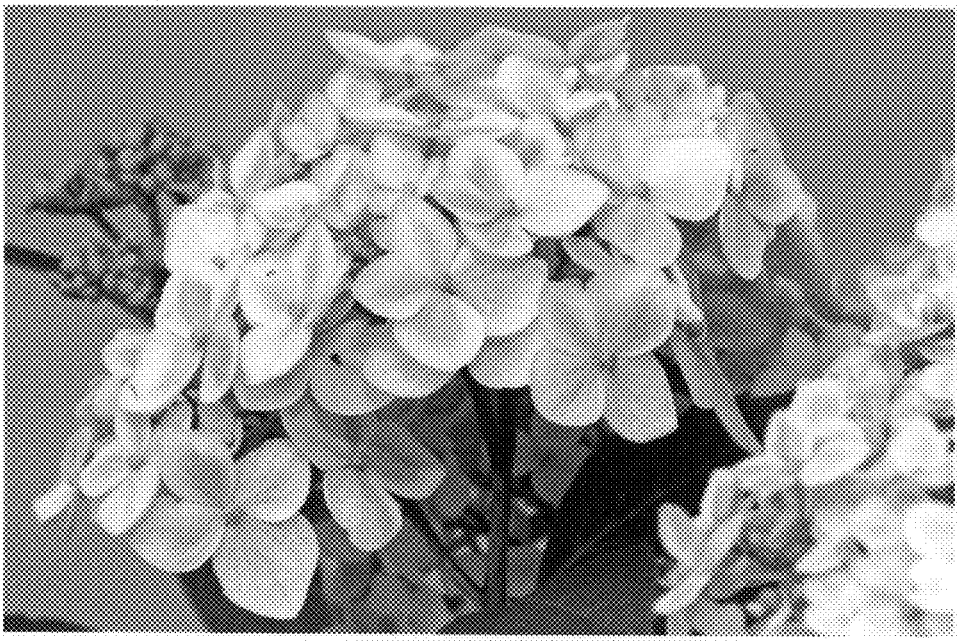

The photograph in FIG. 2 provides a close-up view of an inflorescence of 'KAMOSERE ARIGATOU'.

Figure 3:
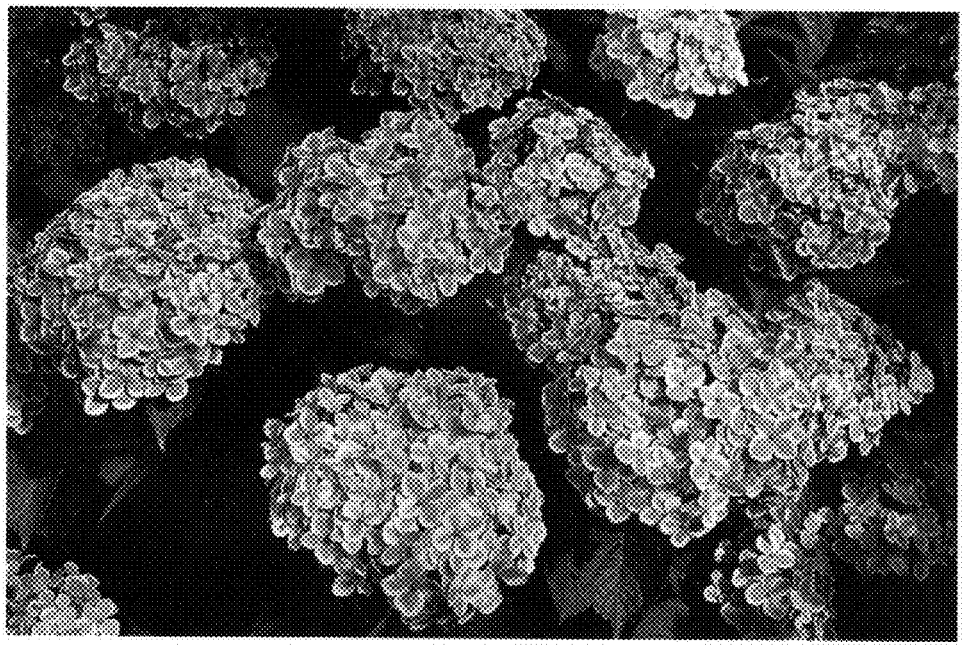

The photograph in FIG. 3 was taken of a plant about 2 years in age as grown in a greenhouse under acidic soil conditions with sufficient aluminum in Kakegawa-City, Shizuoka, Japan.

The colors in the photographs may differ slightly from the color values cited in the detailed botanical description, which accurately describe the colors of the new *Hydrangea*.

BOTANICAL DESCRIPTION OF THE PLANT

The following is a detailed description of characteristics of two year-old plants of the new *Hydrangea* as grown in a greenhouse under alkaline condition in 14-cm containers in Reeuwijk, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Blooms from late spring to late summer in Reeuwijk, The Netherlands.

*Plant type.*—Deciduous shrub, hortensia type *Hydrangea*.

*Plant habit.*—Broadly upright, well-branched.

*Height and spread.*—Reaches an average of 44.3 cm in height and 36.5 cm in width.

*Hardiness.*—At least in U.S.D.A. Zones 5 to 9.

*Diseases resistance.*—No susceptibility or resistance has been observed.

*Root description.*—Fine.

Growth and propagation:

*Propagation.*—Softwood stem cuttings, an average of 10 months from propagation to flowering plant.

*Growth rate.*—Moderate.

Stem description:

*Stem shape.*—Round, solid.

*Stem strength.*—Strong.

*Stem color.*—Young growth; 144B, mature growth; 199C to 199D.

*Stem size.*—An average of 26.2 cm in length (excluding inflorescence) and 6 mm in diameter.

*Stem surface.*—Glabrous and glossy.

*Internode length.*—An average of 6.5 cm.

*Branching.*—An average of 5 lateral branches on a one year-old plant.

Foliage description:

*Leaf shape.*—Elliptic to obovate.

*Leaf arrangement.*—Opposite.

*Leaf division.*—Simple.

*Leaf number.*—An average of 6 per lateral branch.

*Leaf base.*—Cuneate.

*Leaf apex.*—Apiculate to broad apiculate.

*Leaf margins.*—Serrate.

*Leaf venation.*—Pinnate, color; upper surface 144B and lower surface 144C.

*Leaf size.*—An average of 10.3 cm in length and 5.9 cm in width.

*Leaf attachment.*—Petiolate.

*Leaf surface.*—Upper and lower surface; smooth, glabrous, and moderately rugose.

*Leaf color.*—Young foliage upper surface; 137B, young and mature foliage lower surface; 138B mature foliage upper surface; 137A.

*Petioles.*—An average of 1.6 cm in length and 3 mm in diameter, 144B to 144C in color, smooth, moderately glossy surface.

Inflorescence description:

*Inflorescence type.*—Terminal compound corymb, hortensia in form comprised of a center region of fertile flowers surrounded a greater quantity of sterile flowers.

*Lastingness of inflorescence.*—Persistent but color is retained for about 6 weeks.

*Inflorescence number.*—One per lateral or sublateral stem if pinched.

*Inflorescence size.*—An average of 18.9 cm in height (including peduncle) and 9.8 cm in height (excl. peduncle) and 17.2 cm in width.

*Flower number.*—Average of 160 sterile flowers and 24 fertile flowers per panicle.

*Flower fragrance.*—None.

*Flower aspect.*—Upright to outward and slightly drooping.

*Flower size.*—Sterile flowers; average of 3.1 cm in diameter and 6 mm in depth, fertile flowers; average of 8 mm in diameter and 6 mm in depth.

*Flower type.*—Rotate.

*Flower buds.*—Sterile flowers; average of 5 mm in length and 3 mm in diameter prior to opening, ovate in shape, 145A in color prior to opening, fertile flowers; average of 3 mm in width and diameter, broad obovate to globular in shape, a blend of 75C and 186D in color.

*Peduncles.*—Strong, average of 9.1 cm in length and 2.5 mm in width, average angle of 15° from vertical, a mix of 199C to 199D and 182B to 182C in color.

*Pedicels.*—Sterile flowers; held at an average angle of 50° angle from peduncle, an average of 2.2 cm in length and 1.5 mm in width, 182B to 182C in color, surface; dull and moderately covered with thin hairs an average of 0.2 mm in length, fertile flowers; held at an average angle of 15° from vertical, an average of 3 mm in length and 1 mm in width, surface; dull and glabrous, 182C in color.

*Petals.*—Fertile flowers; average of 5, rotate in arrangement, ovate to concave in shape, entire margin, acute apex, cuneate base, average of 3 mm in length and 1.75 mm in width, upper and lower surfaces are smooth and dull, color; upper surface when opening 76C and lower surface when opening 75B, petals drop when mature, sterile flowers; average of 4, rotate in arrangement, ovate to concave in shape, acute apex, cuneate base, entire margin, and average of 2.5 mm in length and 1.3 mm in width, color; upper surface when opening 76C, lower surface when opening and when fully open 75B, upper surface when fully open 76B, upper and lower surface glabrous and dull.

*Sepals.*—Sterile flowers; average of 4, rotate in arrangement, weakly overlapping elliptic in shape, an average of 1.5 cm in length and 1.3 cm in width, obtuse apex, broad acuminate base, upper and lower surface smooth and dull, entire margins, color; upper surface when opening; 75B with margin NN155C and lower surface; 75B to 75C with margin NN155C, color upper surface when fully opened; 75A to 75B with base 72C and margin NN155C and lower surface;

75B to 75C with margin NN155C, color fades to 75D with NN155C on both surfaces, fertile flowers; average of 5, ovate to deltoid in shape, entire margin, acute apex, broad cuneate base, average of 1 cm in length and 1 mm in width, upper and lower surfaces are smooth and dull, color of upper and lower surface when opening and when fully opened 150D.

Reproductive organs: (fertile flowers):

*Stamens.*—Average of 10, anther is broad kidney-shaped, 1 mm in length and 155B in color, filament is 3 mm in length and 71B n color, pollen is moderate in quantity and 156D in color.

*Pistils.*—Average of 3, average of 1.5 mm in length, stigma is club-shaped and 75B in color, style is an average of 1 mm in length and 70B in color, ovary is 70B in color.

*Fruit and seed.*—Has not been observed under the conditions tested to date.

It is claimed:

1. A new and distinct cultivar of *Hydrangea* plant named 'KAMOSERE ARIGATOU' substantially as herein illustrated and described.

* * * * *